(12) United States Patent
Steiger (10) Patent No.: US 11,562,824 B2
(45) Date of Patent: Jan. 24, 2023

(54) PORTABLE DEVICE, METHOD AND SYSTEM FOR COLLECTING AND PROCESSING CONTINUOUS MONITORING DATA INDICATIVE OF AN ANALYTE IN A BODILY FLUID

(71) Applicant: Roche Diabetes Care, Inc., Indianapolis, IN (US)

(72) Inventor: Bernd Steiger, Roemerberg (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 536 days.

(21) Appl. No.: 15/853,020

(22) Filed: Dec. 22, 2017

(65) Prior Publication Data
US 2018/0137939 A1  May 17, 2018

Related U.S. Application Data

(63) Continuation of application No. PCT/EP2016/065482, filed on Jul. 1, 2016.

(30) Foreign Application Priority Data

Jul. 1, 2015  (EP) .................................... 15174913

(51) Int. Cl.
*G16H 40/63* (2018.01)
*H04L 67/12* (2022.01)
(Continued)

(52) U.S. Cl.
CPC .............. *G16H 40/63* (2018.01); *A61B 5/00* (2013.01); *A61B 5/0015* (2013.01);
(Continued)

(58) Field of Classification Search
CPC .... G16H 40/63; A61B 5/0015; A61B 5/6801; A61B 5/00; A61B 5/14532; A61B 5/74;
(Continued)

(56) References Cited

U.S. PATENT DOCUMENTS 7,946,984 B2 * 5/2011 Brister ............... A61B 5/14503
600/365
8,579,853 B2  11/2013 Reggiardo et al.
(Continued)

OTHER PUBLICATIONS

Bluetooth Pairing Part 1—Pairing Feature Exchange, SIG Group, https://www.bluetooth.com/blog/bluetooth-pairing-part-1-pairing-feature-exchange/ (this site discusses Bluetooth ver 4.0 which was released in 2011). (Year: 2016).*
(Continued)

*Primary Examiner* — Jacqueline Cheng
*Assistant Examiner* — Tho Q Tran
(74) *Attorney, Agent, or Firm* — Bose McKinney & Evans LLP (57) ABSTRACT

Disclosed is a portable device for collecting and processing continuous monitoring data. The device has a data interface configured to receive a stream of continuous monitoring data from a body-worn sensor, the continuous monitoring data being indicative of an analyte in a bodily fluid. A control is connectable to the data interface. The control controls a first mode of operation during which configuration parameters are established in response to receiving a start signal indicating a sensor session start of the body-worn sensor. The control also controls a second mode of operation during which the continuous monitoring data is collected and processed and also controls the switching from the first mode to the second mode. The control blocks further starting of the first mode for a remaining sensor session time after the switching to the second mode of operation. Also disclosed are a related medical system, method and computer program product.

24 Claims, 2 Drawing Sheets

(51) Int. Cl.
*A61B 5/00* (2006.01)
*G16H 40/67* (2018.01)
*A61B 5/145* (2006.01)
*A61B 5/1495* (2006.01)
*G06F 21/62* (2013.01)
*H04B 1/3827* (2015.01)
*G06F 21/44* (2013.01)

(52) U.S. Cl.
CPC ........ *A61B 5/14532* (2013.01); *A61B 5/6801* (2013.01); *G06F 21/44* (2013.01); *G16H 40/67* (2018.01); *H04L 67/12* (2013.01); *A61B 5/1495* (2013.01); *A61B 5/74* (2013.01); *G06F 21/6245* (2013.01); *H04B 1/3827* (2013.01)

(58) Field of Classification Search
CPC ... A61B 5/1495; A61B 5/145; G06F 19/3418; G06F 21/44; G06F 21/6245; H04L 67/12; H04B 1/3827
See application file for complete search history.

(56) References Cited

U.S. PATENT DOCUMENTS

| | | |
|---|---|---|
| 8,849,458 B2 | 9/2014 | Weinert et al. |
| 2005/0009126 A1* | 1/2005 | Andrews ................. C12Q 1/54 435/14 |
| 2008/0119702 A1* | 5/2008 | Reggiardo .............. G06F 19/00 600/345 |
| 2011/0022191 A1 | 1/2011 | Amit et al. |
| 2011/0040247 A1* | 2/2011 | Mandro ............ A61M 5/14244 604/66 |
| 2011/0160549 A1* | 6/2011 | Saroka ..................... A61B 5/00 343/700 R |
| 2011/0320130 A1* | 12/2011 | Valdes ................ G06F 19/3418 702/19 |
| 2012/0108934 A1 | 5/2012 | Valdes et al. |
| 2013/0061055 A1* | 3/2013 | Schibuk ............... G06Q 20/223 713/172 |
| 2013/0328572 A1* | 12/2013 | Wang ................... A61B 5/0537 324/601 |
| 2014/0095577 A1 | 4/2014 | Root et al. |
| 2014/0148659 A1 | 5/2014 | Sloan et al. |
| 2014/0200426 A1 | 7/2014 | Taub et al. |
| 2015/0051922 A1 | 2/2015 | Rentas et al. |
| 2016/0367202 A1* | 12/2016 | Carter ................ A61B 5/02416 |

OTHER PUBLICATIONS

International Search Report and Written Opinion of the International Searching Authority, PCT/EP2016/065482, dated Sep. 9, 2016, 12 pages.
Written Opinion of the International Preliminary Examining Authority, PCT/EP2016/065482, dated May 19, 2017, 7 pages.
International Preliminary Report on Patentability, PCT/EP2016/065482, dated Jul. 19, 2017, 20 pages.

* cited by examiner

PORTABLE DEVICE, METHOD AND SYSTEM FOR COLLECTING AND PROCESSING CONTINUOUS MONITORING DATA INDICATIVE OF AN ANALYTE IN A BODILY FLUID

RELATED APPLICATIONS

This application is a continuation of PCT/EP2016/065482, filed Jul. 1, 2016, which claims priority to EP 15174913.2, filed Jul. 1, 2015, both of which are hereby incorporated herein by reference in their entirety.

BACKGROUND

The present disclosure relates to a portable device and a method for collecting and processing continuous monitoring data indicative of an analyte in a bodily fluid, a medical system and a computer program product U.S. Pat. No. 8,849,458 B2 discloses a portable collection device for a structured collection procedure via spot monitoring. A schedule of collection events provides a request to the user for measurement of a biomarker value under defined conditions. A view flag having a viewable value and a non-viewable value is associated with each of the collection events. Non-viewable values are only visible to an authorized user such as a clinician. The authorization is realized via password, encryption or authorization code sent from a computer or a server.

U.S. Publication No. 2014/0200426 A1 describes an in vivo analyte monitoring system including a Professional Options screen where the user can access restricted features that should only be accessed by trained health care professionals (HCP). Therefore, a password or code only given to the HCP's may be required to access the settings. Features that may be restricted are the activation and setting of an insulin calculation feature, a masked mode operation of the device, the resetting of the system and/or settings on the device, etc.

U.S. Pat. No. 8,579,853 B2 discloses infusion devices as well as in vitro or in vivo analyte monitoring devices that are supervisor-controllable or user-restrictive. Configurations of a medical devices are settable and/or lockable by a supervisor (e.g., a HCP—Health Care Professional, parent or guardian, caregiver, or the like), e.g., remotely or by direct action (e.g., using a user interface of the device, or the like). For example, certain configurations of a medical device may be settable and/or lockable by a first person (e.g., a HCP) having a first access level (e.g., full access such as full Read/Write permission) and certain configurations that may be settable and/or lockable by a second person (e.g., a caregiver) having a second access level (e.g., limited Read/Write permission). A user may also be completely restricted from modifying the configurations set by the HCP and/or caregiver.

U.S. Publication No. 2014/0148659 A1 describes systems related to in vivo analyte monitoring that are configurable to switch between a plurality of different modes or configurations. An on-body electronics unit switches between at least two different settings or uses, and the given setting can be determined by the on-body unit and communicated to an analyte monitoring device. One type of use provides for the analyte monitoring device to be configured to operate in a masked mode, and a second type of use provides for the analyte monitoring device to be configured to operate in an un-masked mode.

SUMMARY

This disclosure teaches improved technologies for collecting and processing, in a portable device, continuous monitoring data indicative of an analyte in a bodily fluid and teaches improved usability of the portable device.

According to an aspect, a portable device for collecting and processing continuous monitoring data indicative of an analyte in a bodily fluid is provided. The portable device comprises a data interface device which is configured to receive a stream of continuous monitoring data from a sensor device provided with a body-worn sensor, the continuous monitoring data being indicative of an analyte in a bodily fluid. Further, the portable device comprises a control device which is, at least for data exchange, functionally connectable to the data interface device. The control device is configured to control a configuration mode comprising setting-up configuration parameters for a data collection and processing mode, and process the continuous monitoring data at least during the data collection and processing mode. The control device is further configured to switch from a first to a second mode of operation after finishing the first mode of operation, the first mode of operation comprising starting the configuration mode in response to receiving a start signal indicating a sensor session start of the body-worn sensor, and the second mode of operation comprising the data collection and processing mode and blocking further start of the configuration mode for a remaining sensor session time after switching to the second mode of operation.

According to another aspect, a medical monitoring system is provided comprising a sensor device provided with a sensor to be worn on a body, and a portable device for collecting and processing continuous monitoring data indicative of an analyte in a bodily fluid, wherein, for at least unidirectional data exchange, a data interface of the sensor device and a data interface of the portable device are connectable by a data transmission connection.

According to a further aspect, a method for collecting and processing continuous monitoring data indicative of an analyte in a bodily fluid in a portable device is provided. The method comprises: controlling operation by a control device, at least for data exchange, functionally connectable to a data interface device; receiving a start signal indicating a sensor session start of a body-worn sensor of a sensor device; in response to receiving the start signal, controlling a first mode of operation by the control device, the first mode of operation comprising starting a configuration mode comprising setting-up configuration parameters for a data collection and processing mode; and switching from the first mode of operation to a second mode of operation comprising the data collection and processing mode and blocking further start of the configuration mode for a remaining sensor session time after switching to the second mode of operation.

Another aspect refers to a computer program product, preferably stored on a storage medium and configured to perform a method for collecting and processing continuous monitoring data indicative of an analyte in a bodily fluid during operation on a portable device.

The sensor may be a disposable sensor which may also be referred to as single use sensor. The body-worn sensor may be a sensor for collecting in vivo sensor data.

The configuration mode may be solely started upon or in response to receiving the start signal. Start or invocation of the configuration mode may be automatically without requesting user interaction with the portable device.

The remaining sensor session time after switching to the second mode of operation is without starting (again) the configuration mode. During the course of the sensor session there is a one-time switching process only. Any further start of the configuration mode is prevented. The sensor session of the body-worn sensor may refer to a life cycle or life time of the sensor. The life cycle may be started by connecting the sensor to the portable device for the first time which may also be referred to as pairing the sensor and the portable device. The life cycle may end at the time of disconnecting the sensor from the portable device.

The first mode or operation may be finished in response to receiving user input.

The medical monitoring system may be provided as a continuous glucose monitoring (CGM) system.

The control device may be configured to start the configuration mode without requesting authentication data after receiving the start signal. Specifically, the configuration mode may be started and performed without requesting user authentication data.

The control device may be configured to receive user authentication prior to receiving the start signal, the authentication data being valid for more than one sensor session. The authentication data are to be used for more than one body-worn sensor.

The start signal may be indicating connection of the body-worn sensor to a sensor base of the sensor device. For example, a new disposable sensor may be connected to the sensor base. Connecting may be done be establishing a cable connection between the portable device and the sensor device. As an alternative, a wireless connection may be established.

The start signal may be indicating a request for device connecting received from the sensor device. The request for device connecting may be indicating a request for device pairing and/or a request for setting-up for data exchange.

The start signal may be indicating providing initiation data from the sensor device in the portable device.

The configuration parameters may comprise at least one of a data transfer restricting parameter, a data accessibility parameter, and an interface device control parameter.

The portable device may receive the continuous monitoring data from a body-worn sensor unit via a wireless connection. Interface devices or modules for such wireless communication may be operable under the Bluetooth, in particular the Bluetooth Low Energy Standard. For initiation or starting of the sensor session, the sensor may be inserted subcutaneously. Then the portable device and the body-worn sensor unit are paired (specifically, at least exchange of ID information). Configuration parameters which may also be referred to as configuration settings may be applied only, when the new sensor session is successfully initiated. During the sensor session the sensor device comprising the body-worn sensor constantly transmits raw or preprocessed data to the portable device, where it is processed further depending on the configuration parameters.

The configuration settings may include controlling, specifically restricting, data transfer and data accessibility for each sensor session, such aspect of the configuration being implemented by setting the data transfer restricting parameter and/or the data accessibility parameter. For example, the configuration tool provided on the portable device may control interfaces to be enabled and/or disabled (receiving sensor data over a sensor interface is allowed, but receiving data via other interfaces e.g., for WLAN connectivity is blocked; data is not displayed and screen is permanently locked via passcode). Restrictions of functionality may particularly be useful when facilitating a smartphone as portable device. The data transfer restricting parameter may be configured to restrict data transfer to one or more interfaces selected from a group of interfaces provided in the portable device.

As an alternative or in addition, the interface device control parameter may be set. The interface device control parameter, for example, may be configured to turn on/off an interface provided in the portable device, such configuration may also be referred to as enabling/disabling an interface.

Furthermore, the restrictions in data accessibility, such aspect of the configuration being implementable by setting the data accessibility parameter, may be realized via authentication data, which, for example, may be provided on a very first launch for all sensor sessions and which may be used for different purposes. The data accessibility parameter may be configured to implement at least one of lock/unlock screen, deactivate software, encrypt/decrypt data, access system configurations like adjust speaker volume, and alert or alarm thresholds. The authentication data may be used to encrypt collected sensor data. Such encrypted data may be transferred to another system, where the HCP provides authentication data for decryption. Additionally or alternatively, the configuration software can set configuration parameters assigned to control switches to disable de-installation of the configuration software from the portable device. Instead the device may enter a deactivated mode and may only be locked via the authentication data while the software remains in memory. These functionalities may simplify operation of the HCP's portable device for different patients.

The patient individual configuration parameters are only accessible at each start of operation of the system and used as new system settings only if the action providing the start signal to be received in the portable device was completed successfully. Furthermore, the action providing the start signal, e.g., pairing of the CGM remote controller with a CGM transmitter, may be successfully completed only if the action provides new information, e.g., the CGM remote controller receives from the re-usable CGM transmitter the information that a new CGM sensor has been used). In case the procedure could not be completed successfully the system settings (configuration parameters) are not updated and therefore, for example, may prevent that the patient can change such HCP customizable patient individual setting.

Data (encrypted or not) collected in the portable device can be transferred to a data evaluation system. In order to limit the access to the encrypted data, the encrypted data may be automatically decrypted only if a PIN is stored in the data evaluation system. The access to not encrypted data or decrypted data may not be limited by setting the data accessibility parameter.

The control device may be provided with a control module (module) configured to suppress amendment of the configuration parameters set in the configuration mode. The control module implementable as a software module may be running permanently during operation of the portable device, e.g., as a background application not visible to the user, but at least during both the configuration mode and the data collection and processing mode. In addition or as an alternative, the control module may be configured to suppress amendment of another configuration parameter set for operation of the portable device, but not set in the configuration mode. The at least one other configuration parameter defining a feature of device operation may be a pre-configured parameter or a parameter configurable by the user.

The different aspects of the disclosure may be applied for in vivo continuous glucose monitoring (CGM) configuration. Configuration is only possible when a new CGM session is started (e.g., by subcutaneous insertion of a new sensor or by pairing of the body-mounted sensor unit with the portable device). For example, in the configuration mode the user, e.g., the HCP, can customize patient individual settings on the portable device upon start of every new session. This way applying a password protected setup menu or transferring configuration parameters or the distribution of the configuration software respective the corresponding software product key may be avoided.

Furthermore, a blinded, mixed and/or un-blinded mode may be set. The un-blinded mode of operation comprises displaying the continuous monitoring data on the display device of the portable device. On the other hand the blinded mode of operation at least comprises storing the continuous monitoring data in a storage device of the portable device, but blocking displaying of the continuous monitoring data on the display device. The blinded mode of operation is characterized by not displaying the continuous monitoring data on the display device, therefore, not "disclosing" the continuous monitoring data via the display device to the user of the portable device. The mixed mode refers to a scheme of operation comprising operating the portable device according to both the un-blinded and the blinded mode of operation during one and same sensor session.

The blocking of displaying the continuous monitoring data on the display device may comprise blocking of providing the video data indicative of the continuous monitoring data in the portable device. As an alternative, the video data indicative of the continuous monitoring data may still be processed in the portable device, but outputting of the video data on the display is prevented. The video data processed in the portable device may be stored in a storage device of the portable device in at least one of the first and second mode of operation.

A portable device for processing continuous monitoring data indicative of an analyte in a bodily fluid may be provided. The portable device may comprise a data interface device which is configured to receive a stream of continuous monitoring data from a body-worn sensor, the continuous monitoring data being indicative of an analyte in a bodily fluid. Further, the portable device comprises a storage device which is configured to store the continuous monitoring data at least in part, and a control device which is configured to process the continuous monitoring data and, at least for data exchange, functionally connectable to the data interface device, and the storage device. The control device is further configured to switch, according to a predefined operation condition, between a first and a second mode of operation during a sensor session of the body-worn sensor, the first mode operation comprising providing video data indicative of the continuous monitoring data for outputting the video data by a display device, and the second mode of operation comprising storing the continuous monitoring data in the storage device and blocking displaying of the continuous monitoring data on the display device.

According to another aspect, a medical monitoring system is provided, comprising a sensor device to be worn on a body, and a portable device for processing continuous monitoring data indicative of an analyte in a bodily fluid, wherein, for at least unidirectional exchanging data, a data interface of the sensor device and a data interface of the portable device are connectable by a data transmission connection.

Further, a method for processing continuous monitoring data indicative of an analyte in a bodily fluid in a portable device is provided. The method comprises: controlling operation by a control device, at least for data exchange, functionally connectable to a data interface device, and a storage device; receiving a stream of continuous monitoring data from a body-worn sensor via a data interface device; processing the continuous monitoring data in the control device; and switching, according to a predefined operation condition, between a first and a second mode of operation during a sensor session of the body-worn sensor, the first mode operation comprising providing video data indicative of the continuous monitoring data for outputting the video data by a display device, and the second mode of operation comprising storing the continuous monitoring data in the storage device at least in part and blocking displaying of the continuous monitoring data on the display device.

In an embodiment, the analyte to be determined may be glucose. Continuous monitoring data indicative of glucose in the bodily fluid may be provided, specifically, blood glucose.

The medical monitoring system may be provided as a continuous glucose monitoring (CGM) system.

The body-worn sensor may be a sensor for collecting in vivo sensor data. The body-worn sensor may be a continuous monitoring sensor, specifically a continuous glucose monitoring sensor configured to be provided in the interstitium.

The sensor session of the body-worn sensor may refer to a life cycle or life time of the sensor. The life cycle may be started by connecting the sensor to the portable device for the first tile which may also be referred to as pairing the sensor and the portable device. The life cycle may end at the time of disconnecting the sensor from the portable device.

In the first mode operation displaying of the continuous monitoring data on the display device may be provided as real-time displaying.

The blinded mode of operation may be used by HCPs (Health Care Professionals) which apply continuous monitoring, e.g., CGM, for diagnostic purposes. They prefer to derive therapy adaptions based on measured patterns, e.g., glucose patterns, and profiles which are not altered by behavioral changes of the patient due to monitoring information disclosed to the user or patient. On the other hand professional continuous monitoring systems may also be used for educational purposes allowing patients to learn more about physiological effects to nutrition, exercise, illness, insulin dosing, etc. In these cases the system is used in un-blinded mode.

The operation of the portable device in the first and second mode of operation during the sensor session may be referred to as a mixed mode of operation. It allows for a controlled switching between the blinded and un-blinded mode for one and the same sensor device during its lifetime or during a running sensor session. In particular, the HCP may set a specified time period on the portable device, such that after the specified time period the mode of operation is automatically switched to un-blinded or blinded mode. Such option for combined use, for example, allows for a single CGM-sensor to be used for both professional (blinded) and personal (un-blinded) cases. This gives the user and the HCP more flexibility and makes the CGM system more comfortable and cost-efficient. This combination of modes is particularly useful in view of CGM systems with extended sensor lifetimes, e.g., a sensor lifetime of more than 14 days.

The continuous monitoring data not displayed in the second mode of operation may be provided for a retrospective analysis, e.g., only for HCPs.

The term video data as used to in the present disclosure refers to data which can be outputted over a display device.

The predefined operation condition may define one or more switching conditions. Switching between the first and second mode of operation may be performed if the switching condition(s) is fulfilled. For example, the switching condition(s) may refer to at least one of a fixed switching time, a switching date, a time period, and a period of use of the portable device after completion of which mode switching is performed. In case of having the switching condition(s) fulfilled, prior to actual switching a confirmation may be requested from the user. For example, the user may be requested to provide a confirmation input over a user interface of the portable device. Specifically, a user input may be received over a touch pad of the portable device. At the time of fulfilling the one or more switching conditions the switching may be performed automatically, i.e., without requesting any user input or user response. Specifically by automatic switching procedure, a pattern of switching events may be applied. The switching pattern is defined by the switching conditions.

A user interface device may be provided which is configured to receive a user input defining the predefined operation condition.

The control device may be configured to switch more than once between the first and the second mode of operation during the sensor session. A condition parameter for switching may be defined in response to a user input received in the portable device. The condition parameter, for example, may define a date, a time, a switching frequency, and a period of time. Switch more than once between the first and the second mode of operation may be performed over the course of several sensor sessions.

The control device may be configured to switch between the first and the second mode of operation while the stream of continuous monitoring data is received.

The control device may be configured to process a stream of continuous monitoring in vivo data.

The display device may be provided in the portable device. As an alternative, the display device may be provided separately from the portable device. For outputting the video data may be transmitted from the portable device to the separated display device via a wireless or a wired data transmission connection.

The portable device may be selected from the following group of portable devices: mobile phone, tablet computer, laptop computer, portable medical device, portable medical measurement device, and a smart watch. The portable device may be configured with a software program being downloaded from the internet, for example, in form of a so-called App.

The control device may be configured to output a warning signal during at least one of the first and second mode of operation. The warning signal may be at least one of a visual signal and an audio signal. For example, a warning signal may be outputted if continuous glucose data processed from the continuous glucose monitoring data provide indication of a hypo- or hyperglycemia. During processing of the continuous monitoring data in the control device the warning signal may be provided for output if the continuous glucose monitoring data traverse or cross a threshold value provided in the control device. For example, a threshold for the blood glucose level may be provided. In a mode of operation, the warning signal is outputted without displaying video data indicative of the continuous glucose monitoring data traversing the threshold value (second mode of operation).

The control device may be configured to display, in the second mode of operation, further video data on the display device, such further video data being different from the video data indicative of the continuous monitoring data. The further video data may be representing event information, e.g., calendar information. The calendar information may be specifying date and/or time information. With regard to the user of the portable device, the calendar information may refer to events like insulin intake, carbohydrate intake, physical activity, and/or illness. As an alternative or in addition, the further video data may be representing a result of a spot monitoring provided by a non-continuous blood glucose measurement. The portable device may be configured for non-continuous blood glucose measurement, e.g., by having a sensor device configured to analyze a test or control strip. In the portable device, the further video data and/or measurement data representing the result of the spot monitoring may be received from a measurement device, e.g., by wireless data transmission. From the measurement data received in the portable device the further video data may be derived by data processing.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
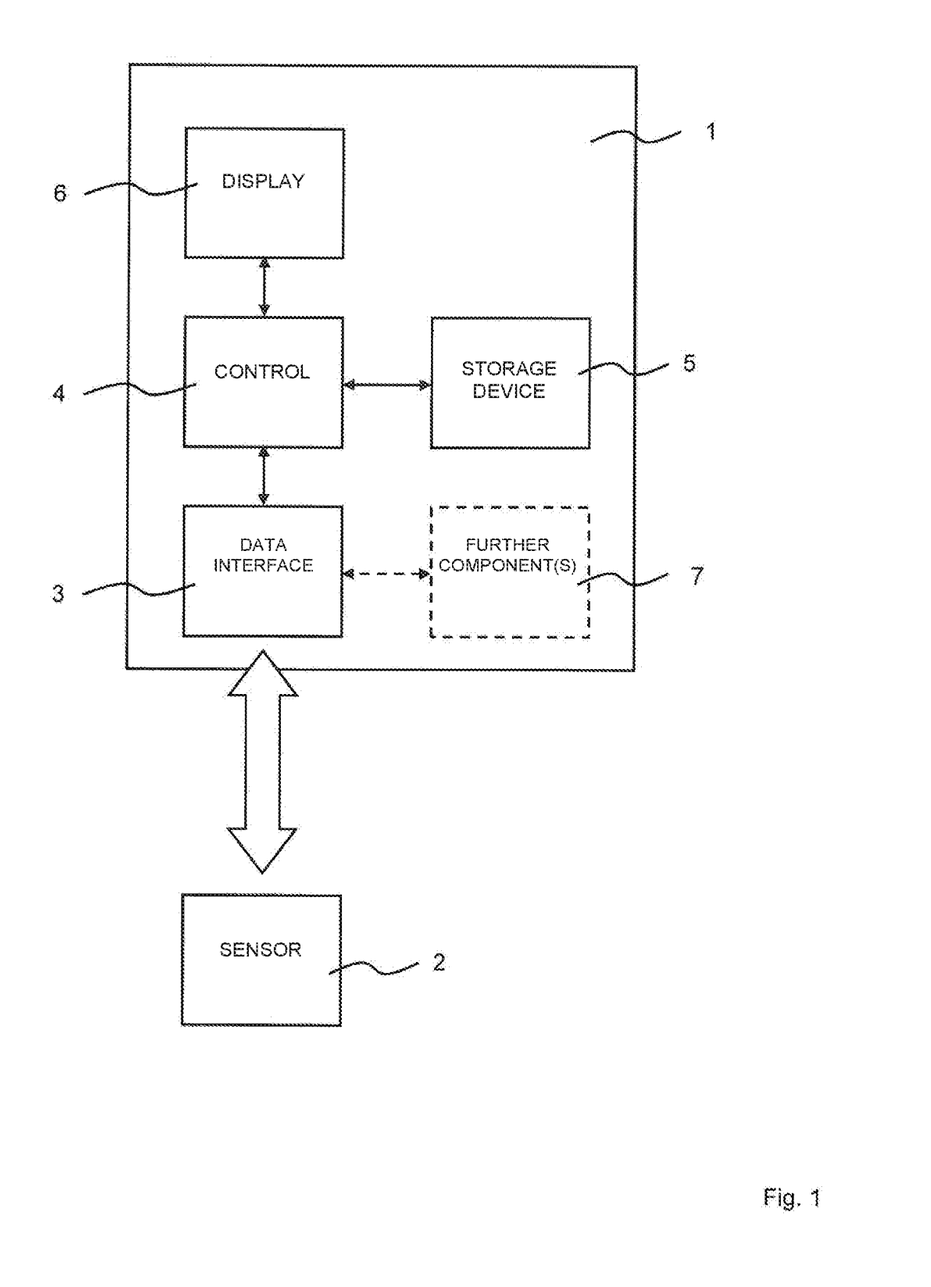
FIG. 1 is a schematic representation of an arrangement with a portable device and a sensor device to be worn on a body.

FIG. 1 shows a schematic representation of an arrangement with a portable device 1 and a sensor device or sensor 2 provided with a sensor to be worn by a patient (body-worn). The portable device is provided with a data interface device or data interface 3, a control device or control 4, a storage device 5, and a display device or display 6. The control device 4, at least for unidirectional data transmission, is connected to or in communication with the data interface device 3, the control device 4, the storage device 5, and the display device 6. Further functional components 7 may be provided.

Data transmission between the portable device 1 and the sensor device or sensor 2 may be provided by wireless and/or wired data transmission. Typically the portable device 1 receives data from the body-worn sensor device 2 via a wireless connection. Preferred interfaces for such wireless communication are operable under Bluetooth or Bluetooth Low Energy Standard. On initiation of the sensor session, the portable device 1 and the body-worn sensor device 2 are paired (specifically, exchange of ID information) and during the sensor session the body-worn sensor device 2 may constantly transmit raw or preprocessed monitoring data to the portable device 1, where it may be either stored and displayed or only stored and not displayed.

Figure 2:
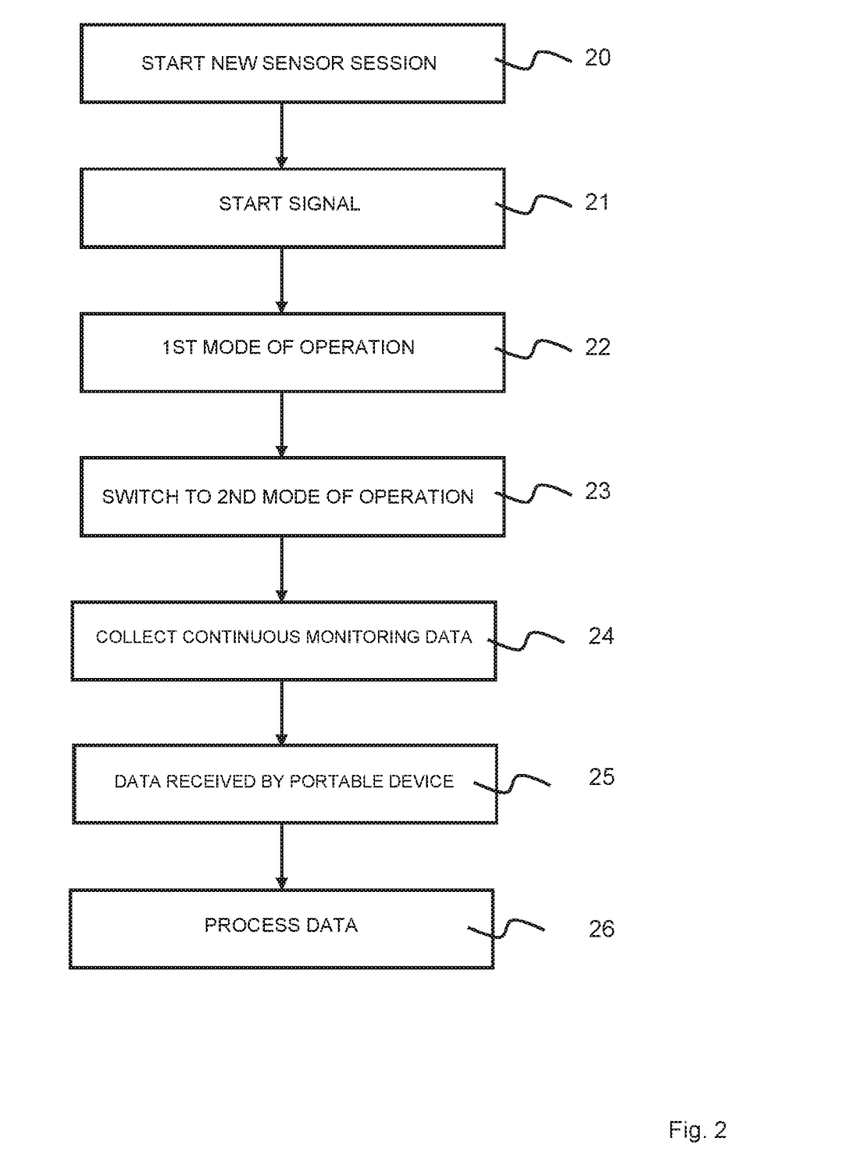
FIG. 2 is a schematic representation for a method for collecting and processing continuous monitoring data indicative of an analyte in a bodily fluid in the portable device.

FIG. 2 shows a schematic representation for a method for collecting and processing continuous monitoring data indicative of an analyte in a bodily fluid in the portable device 1. In step 20, a new sensor session is started for sensor of the sensor device 2. In response to the session beginning, e.g., in response to connecting the sensor to a base unit of the sensor device 2, a start signal indicating start of the new sensor session is received in the portable device 1 (step 21). In response to receiving the start signal, in step 22, a first mode of operation is controlled by the control device 4 of the portable device, the first mode of operation comprising starting a configuration mode comprising setting-up configuration parameters for a data collection and processing mode to be followed.

In step 23 it is switched from the first mode of operation to a second mode of operation comprising the data collection and processing mode and blocking further start of the configuration mode for a remaining sensor session time after switching to the second mode of operation. During the second mode of operation a stream of continuous monitoring data is collected by the sensor device 2 (step 24). The stream of continuous monitoring data is received in the portable device 1 from the body-worn sensor 2 via the data interface device 3 (step 25). In step 26, the continuous data are processed in the control device 4. During any given sensor session of the body-worn sensor 2 it is switched only once from the first to the second mode of operation.

A continuous monitoring data received in the portable device 1 may be preprocessed by the control device 4. Preprocessing data by the control device 4 may for instance include packing the data to reduce communication load and/or calibrating the data according to some reference value(s), e.g., blood glucose reference value(s). Once the data is received by the portable device the processing device may process the data further. E.g., for raw data the processing may include calibration. Additionally, further data analysis such as trend analysis, threshold analysis, error analysis, and/or statistical analysis also may be performed.

The control device 4 of the portable device 1 may be configured to switch between an un-blinded and a blinded mode of operation during a running sensor session depending on a predetermined condition. Such conditions include, e.g., time, glucose thresholds for hypo- or hyperglycemia or other dangerous conditions. As mentioned before, the un-blinded mode comprises to store and not to display the received data stream and the second mode comprises to at least display the received data stream.

The un-blinded mode of operation comprises displaying the continuous monitoring data on the display device of the portable device. On the other hand, the blinded mode of operation at least comprises storing the continuous monitoring data in a storage device of the portable device, but blocking displaying of the continuous monitoring data on the display device. The blinded mode of operation is characterized by not displaying the continuous monitoring data on the display device, therefore, not "disclosing" the continuous monitoring data via the display device to the user of the portable device. A mixed mode of operation refers to a scheme of operation comprising operating the portable device 1 according to both the un-blinded and the blinded mode of operation during one and same sensor session.

The predetermined operation condition defining switching condition may be limited to be set through the portable device only and no distinction may made between sensors depending on their uses. Thus the condition may apply any time after pairing of the portable device with the sensor until the full sensor session has run up.

As simple predetermined operation condition is to set a timer for, e.g., the blinded mode and switch to un-blinded mode after time has run out. Alternatively or additionally, the switching may be triggered by exceeding a threshold for a blood glucose level, i.e., if the calibrated value from the continuous monitor exceeds a threshold for hypoglycemia or hyperglycemia. This gives at least some safety net to indicate dangerous conditions to the user despite blinded mode. Further alternatively or additionally, the switching may be triggered via remote access by the HCP. In such an embodiment the data can for instance be remotely accessed by the HCP and as soon as a significant amount of data is gathered the HCP can remotely enable un-blinded mode. Such remote access may be encrypted for safety reasons.

The blinded mode includes storing and not displaying data, specifically calibrated data. However, some analysis may already be done on the not-displayed data and stored, e.g., trend analysis, threshold analysis, error analysis, statistical analysis. Also other functions such as alarm functions, warnings and/or bolus calculations may still be available to the user.

In un-blinded mode of operation the user additionally has access via the display to the glucose levels, trend graphs, and other representations of the data collected by the continuous glucose monitor. In both modes it is required to provide for reference blood glucose values for calibration purposes.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A portable device for collecting and processing continuous monitoring data, comprising:
   a data interface configured to receive a stream of continuous monitoring data from a body-worn sensor, the continuous monitoring data being indicative of an analyte in a bodily fluid, and
   a control device in communication with the data interface, wherein the control device is configured to control:
      a first mode of operation during which configuration parameters are established in response to receiving a start signal indicating a sensor session start of the body-worn sensor and wherein establishing the configuration parameters defines at least one parameter controlling collection or processing of the continuous monitoring data;
      a second mode of operation during which the continuous monitoring data is collected and processed;
      switching from the first mode to the second mode; and
      blocking of further starting of the first mode for a remaining sensor session time after the switching to the second mode of operation wherein by such blocking, the switching from the first mode to the second mode occurs only once during the course of the sensor session and any further start of the first mode during the course of the sensor session is prevented, and wherein the first mode of operation is solely invoked in response to receiving the start signal and the first mode of operation is automatically initiated upon receipt of the start signal and the switching from the first mode to the second mode occurs in response to user input.

2. Portable device according to claim 1, wherein the control device is configured to start the first mode without requesting authentication data after receiving the start signal.

3. Portable device according to claim 1, wherein the control device is configured to receive user authentication prior to receiving the start signal, the authentication data being valid for more than one sensor session and wherein the control device is further configured to use the authentication data to encrypt the continuous monitoring data.

4. Portable device according to claim 1, wherein the start signal indicates connection of the body-worn sensor to a sensor base of the sensor device.

5. Portable device according to claim 1, wherein the start signal indicates a pairing request received from the body-worn sensor.

6. Portable device according to claim 1, wherein the start signal indicates the providing of initiation data from the body-worn sensor.

7. Portable device according to claim 1, wherein the configuration parameters comprise a data transfer restricting parameter.

8. Portable device according to claim 1, wherein the configuration parameters comprise a data accessibility parameter.

9. Portable device according to claim 1, wherein the configuration parameters comprise an interface device control parameter.

10. Portable device according to claim 1, wherein the control device is provided with a control module configured to suppress amendment of the configuration parameters set in the configuration mode.

11. Portable device according to claim 1 wherein the control device is configured such that the sensor session time starts after connecting the body-worn sensor to the portable device for the first time and ends when the body-worn sensor is disconnected from the portable device.

12. Portable device according to claim 1 wherein the first mode of operation is only initiated upon receipt of the start signal if an action providing the start signal also provides new information to the control device.

13. Portable device according to claim 12 wherein the new information is information corresponding to the use of a new body-worn sensor.

14. A medical monitoring system, comprising:
a sensor to be worn on a body; and
a portable device, comprising:
a data interface configured to receive a stream of continuous monitoring data from the sensor, the continuous monitoring data being indicative of an analyte in a bodily fluid, and
a control device in communication with the data interface, wherein the control device is configured to control:
(i) a first mode of operation during which configuration parameters are established in response to receiving a start signal indicating a sensor session start of the sensor wherein establishing the configuration parameters defines at least one parameter controlling collection or processing of the continuous monitoring data, (ii) a second mode of operation during which the continuous monitoring data is collected and processed, (iii) switching from the first mode to the second mode; (iv) blocking of further starting of the first mode for the remaining sensor session time after the switching to the second mode of operation wherein by such blocking, the switching from the first mode to the second mode occurs only once during the course of the sensor session and any further start of the first mode during the course of the sensor session is prevented; and (v) wherein the first mode of operation is automatically initiated upon receipt of the start signal and the switching from the first mode to the second mode occurs in response to user input.

15. The system of claim 14, wherein the sensor has a sensor data interface and wherein the sensor data interface and the data interface of the portable device are connectable via a data transmission connection for at least unidirectional exchange of data.

16. Medical monitoring system according to claim 14 wherein the sensor is a single use, disposable sensor having a lifetime and the sensor session time corresponds to the lifetime of the sensor.

17. Medical monitoring system according to claim 16 wherein the lifetime of the sensor starts when the sensor is connected to the portable device for the first time and ends when the sensor is disconnected from the portable device.

18. A method for collecting and processing continuous monitoring data indicative of an analyte in a bodily fluid, comprising:
providing a portable device having a data interface and a control device;
receiving, with the portable device, a start signal indicating a sensor session start of a body-worn sensor;
in response to receiving the start signal, controlling a first mode of operation by the control device, the first mode of operation comprising setting-up configuration parameters for data collection and processing wherein establishing the configuration parameters defines at least one parameter controlling collection or processing of the continuous monitoring data; and
switching from the first mode of operation to a second mode of operation, the second mode comprising the data collection and processing; and
blocking a further start of the first mode for a remaining sensor session time after switching to the second mode of operation wherein by such blocking, the switching from the first mode to the second mode occurs only once during the course of the sensor session and any further start of the first mode during the course of the sensor session is prevented, and wherein the first mode of operation is automatically initiated upon receipt of the start signal and the switching from the first mode to the second mode occurs in response to user input.

19. Computer program product stored on a non-transitory computer readable storage medium wherein the computer program product configures a processor to perform the method according to claim 18 during operation on a portable device.

20. The method of claim 18 further comprising the steps of:
receiving with the portable device, authentication data prior to receiving the start signal and using the authentication data to encrypt the continuous monitoring data; and
transferring the encrypted continuous monitoring data to another system.

21. A portable device for collecting and processing continuous monitoring data, comprising:
a data interface configured to receive a stream of continuous monitoring data from a body-worn sensor, the continuous monitoring data being indicative of an analyte in a bodily fluid, and a control device in communication with the data interface, wherein the control device is configured to control:
  a first mode of operation during which configuration parameters are established in response to receiving a start signal indicating a sensor session start of the body-worn sensor and wherein establishing the configuration parameters defines at least one parameter controlling collection or processing of the continuous monitoring data;
  a second mode of operation during which the continuous monitoring data is collected and processed;
  switching from the first mode to the second mode; and
  blocking of further starting of the first mode for a remaining sensor session time after the switching to the second mode of operation wherein by such blocking, the switching from the first mode to the second mode occurs only once during the course of the sensor session and any further start of the first mode during the course of the sensor session is prevented; and
wherein the configuration parameters comprise a data transfer restricting parameter and the portable device comprises a plurality of interfaces configured for data transfer and wherein the data transfer restricting parameter is configured during the first mode of operation to restrict receipt of continuous monitoring data from the sensor to only one of the plurality of interfaces.

22. A portable device for collecting and processing continuous monitoring data, comprising:
  a data interface configured to receive a stream of continuous monitoring data from a body-worn sensor, the continuous monitoring data being indicative of an analyte in a bodily fluid, and
  a control device in communication with the data interface, wherein the control device is configured to control:
    a first mode of operation during which configuration parameters are established in response to receiving a start signal indicating a sensor session start of the body-worn sensor and wherein establishing the configuration parameters defines at least one parameter controlling collection or processing of the continuous monitoring data;
    a second mode of operation during which the continuous monitoring data is collected and processed;
    switching from the first mode to the second mode; and
    blocking of further starting of the first mode for a remaining sensor session time after the switching to the second mode of operation wherein by such blocking, the switching from the first mode to the second mode occurs only once during the course of the sensor session and any further start of the first mode during the course of the sensor session is prevented; and
  wherein the data configuration parameters comprise an interface device control parameter and the portable device comprises a plurality of interfaces configured for data transfer and wherein the interface device control parameter is configured during the first mode of operation to enable only one of the plurality of interfaces to receive continuous monitoring data from the sensor.

23. A portable device for collecting and processing continuous monitoring data, comprising:
  a data interface configured to receive a stream of continuous monitoring data from a body-worn sensor, the continuous monitoring data being indicative of an analyte in a bodily fluid, and
  a control device in communication with the data interface, wherein the control device is configured to control:
    a first mode of operation during which configuration parameters are established in response to receiving a start signal indicating a sensor session start of the body-worn sensor and wherein establishing the configuration parameters defines at least one parameter controlling collection or processing of the continuous monitoring data;
    a second mode of operation during which the continuous monitoring data is collected and processed;
    switching from the first mode to the second mode; and
    blocking of further starting of the first mode for a remaining sensor session time after the switching to the second mode of operation wherein by such blocking, the switching from the first mode to the second mode occurs only once during the course of the sensor session and any further start of the first mode during the course of the sensor session is prevented, and wherein switching between the first mode of operation and the second mode of operation is only permitted if a predefined operation condition is satisfied and upon receipt of user confirmation input received by a user interface of the portable device.

24. Portable device according to claim 23 wherein the predefined operation condition is one of the group consisting of a fixed switching time, a switching date, a time period and a period of use of the portable device.

* * * * *